United States Patent [19]

Potthast et al.

[11] 4,354,038
[45] Oct. 12, 1982

[54] PROCESS FOR THE PREPARATION OF 3-HYDROXYBENZOIC ACID

[75] Inventors: Ruthard Potthast, Leverkusen; Werner Mentzel, Cologne; Horst-Dieter Kramer, Leverkusen, all of Fed. Rep. of Germany

[73] Assignee: Bayer Aktiengesellschaft, Leverkusen, Fed. Rep. of Germany

[21] Appl. No.: 257,676

[22] Filed: Apr. 27, 1981

[30] Foreign Application Priority Data

May 10, 1980 [DE] Fed. Rep. of Germany ....... 3017983

[51] Int. Cl.$^3$ ............................................. C07C 65/03
[52] U.S. Cl. .................................................. 562/475
[58] Field of Search ......................................... 562/475

[56] References Cited

U.S. PATENT DOCUMENTS 3,099,686  7/1963  Keith et al. .......................... 562/475

*Primary Examiner*—Paul J. Killos
*Attorney, Agent, or Firm*—Sprung, Horn, Kramer & Woods

[57] ABSTRACT

A process for the preparation of an alkali metal salt of 3-hydroxybenzoic acid and the preparation of 3-hydroxybenzoic acid therefrom is disclosed wherein sulphophthalic acid or a salt thereof is reacted with an alkali metal hydroxide at a temperature in the range of 200° to 300° C. at a pressure of 10 to 30 bars.

12 Claims, No Drawings

PROCESS FOR THE PREPARATION OF 3-HYDROXYBENZOIC ACID

The present invention relates to a process for the preparation of an alkali metal salt of 3-hydroxybenzoic acid from sulphophthalic acid and to the preparation of 3-hydroxybenzoic acid itself.

It is known from U.S. Pat. No. 3,094,558 to prepare 3-hydroxybenzoic acid from 3-sulphobenzoic acid in a melt with potassium hydroxide. The 3-sulphobenzoic acid is prepared by sulphonation of benzoic acid with oleum or sulphur trioxide (U.S. Pat. No. 3,094,558, lines 20 to 22). In the case of this industrially customary sulphonation of benzoic acid, the isomeric sulphobenzoic acids are also formed as by-products, in addition to the 3-sulphobenzoic acid as the main product (Ullmann, volume 8, line 380, 4th edition (1974)). The 2- and 4-sulphobenzoic acids obtained as by-products cannot be separated off completely.

The consequence of this is that the potassium hydroxide melt does not yield pure 3-hydroxybenzoic acid but always a mixture of the isomeric hydroxybenzoic acids. Furthermore, 4-hydroxybenzoic acid decarboxylates easily in the potassium hydroxyde melt, so that phenol is also obtained as a further by-product in the industrial preparation of 3-hydroxybenzoic acid.

The said by-products of 3-hydroxybenzoic acid can be separated off only with exceptional difficulty and adversely affect subsequent use of the 3-hydroxybenzoic acid. The latter is an intermediate product in the preparation of plastics and plant protection agents and serves, as the acid or in the form of its simple aliphatic esters, as a plasticizer.

A process for the preparation of 3-hydroxybenzoic acid has been found which is characterized in that sulphophthalic acids of the formula

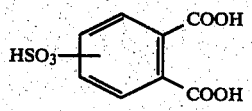

or salts thereof, are reacted with an alkali metal hydroxide in the temperature range of about 200° to 300° C. and in the pressure range of about 10 to 30 bars.

The 3-hydroxybenzoic acid thus obtained is obtained in high yields and free from interfering by-products.

The process according to the invention can be illustrated with the aid of the following reaction

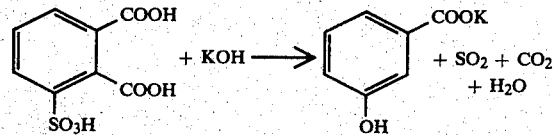

Within the framework of the process according to the invention, sulphophthalic acid are 3-sulphophthalic acid and 4-sulphophthalic acid. They can be reacted according to the invention either on their own or as a mixture, to give 3-hydroxybenzoic acid. Preferably, a mixture of the two isomeric sulphophthalic acids such as is obtained from the sulphonation of phthalic anhydride with oleum is used for the process according to the invention. The mixture obtained from the said sulphonation is a mixture of 3-sulphophthalic acid and 4-sulphophthalic acid in a ratio of 1:4 to 1:6.

Of course, it is also possible to employ salts including partial salts of sulphophthalic acid in the process according to the invention. In general, it is then appropriate to employ the alkali metal salts, for example the sodium salt and/or potassium salt, of sulphophthalic acid.

Alkali metal hydroxides used for the process according to the invention are in general sodium hydroxide and potassium hydroxide. It is, of course, also possible to employ a mixture of sodium hydroxide and potassium hydroxide.

In general, 7 to 18 mols of alkali metal hydroxide, relative to 1 mol of the sulphophthalic acid, are employed for the process according to the invention. Preferably, 10 to 12 mols of alkali metal hydroxide are used, relative to 1 mol of the sulphophthalic acid.

The process according to the invention is in general carried out in the temperature range of about 200° to 300° C. and in the pressure range of about 10 to 30 bars. Preferably, the process according to the invention is carried out in the temperature range of 210° to 280° C. The preferred pressure range for the process according to the invention is 18 to 25 bars. The reaction time is about 5 to 15 hours, preferably 8 to 12 hours.

The sulphophthalic acids can be employed in the process according to the invention in the form of their aqueous solutions. In the case of this preferred embodiment of the process according to the invention, aqueous solutions of the sulphophthalic acid containing from 30 to 70% are generally employed.

The process according to the invention can be carried out, for example, as follows:

An aqueous solution of the alkali metal hydroxide is initially introduced into an autoclave and a mixture of 3-sulphophthalic acid and 4-sulphophthalic acid is introduced into the solution. The reaction mixture is then reacted according to the invention. In general, 8 to 15 hours are required for the reaction.

After the reaction has ended, the melt is cooled and taken up in water. To prepare free 3-hydroxybenzoic acid, the reaction mixture is acidified with a mineral acid, for example hydrochloric acid.

The process can be carried out by acidification of the reaction mixture obtained following treatment of the sulphophthalic acid compound with alkali metal hydroxide. It is unnecessary to isolate the hydroxybenzoic acid alkali metal salt or to work the same up in any particular manner, although the process can be carried out by isolating the alkali metal salt of 3-hydroxybenzoic acid and thereafter acidifying the same with a suitable acid, such as a mineral acid. Acidification conditions for conversion of the alkali metal salt to the free acid include: simple addition of diluted mineral acid to the suspension at room temperature. The resulting slurry subsequently being heated up to about 105° C. and then gradually chilled down to approx. 20° C.

In this way, 3-hydroxybenzoic acid is obtained in virtually quantitative yield with high purity.

3-Hydroxybenzoic acid is, for example, converted to high molecular weight polyesters by reaction with acyl chlorides (4–8 C atoms) under the catalytic influence of zinc chloride (literature: Caldwell, U.S. Pat. No. 2,600,376 (1952)).

Plant protection agents are prepared by nitration of 3-hydroxybenzoic acid to 2-nitro-5-hydroxybenzoic acid and a subsequent condensation reaction with a suitable component to give 4-nitro-2'-chloro-4'-trifluoromethyldiphenyl ether-3-carboxylic acid (literature: Beyer, Rec. trav. chim. 40, 613-23 (1921), C.A. 16, 1230 (1922) and U.S. Pat. No. 4,031,131 (1977)).

EXAMPLES

EXAMPLE 1

403.9 g (content 91.4%) of a mixture of 3-sulphophthalic acid and 4-sulphophthalic acid in the form of its monosodium salt (corresponding to 369 g of 100% ≙ 1.5 mols) are added gradually to 960 g of 50% strength sodium hydroxide solution (12 mols of NaOH), which has been intially introduced. The total volume is about 860 ml.

The mixture warms to about 95° C. and the nickel autoclave, which has a capacity of 1.3 l, is closed and heated at 235° C. for a period of 12 hours. The pressure set up is 17.5 to 18.5 bars. At the end of the reaction time the melt is cooled, emptied from the autoclave and rinsed with 1000 ml of water.

The resulting colourless crystal suspension is warmed to 80° C. and introduced carefully, in the course of 1 hour, into a mixture of 1500 ml of crude concentrated hydrochloric acid and 300 g of ice, whilst stirring. Vigorous evolution of gas, due to the carbon dioxide and sulphur dioxide liberated, is observed. After the introduction is complete, the pH value of the suspension is 0.7 and the temperature of the suspension is 90° C. The residual sulphur dioxide is driven off at a temperature of about 90° C., and the mixture is then cooled to 20° C. It is stirred for a further period of 3 hours.

The completely colouless precipitate which has separated out is filtered off and then washed with 6 portions of, in each case, 100 ml of water.

The resulting product is then dried in a vacuum drying cabinet at 90° C. and under a pressure of 20 mm Hg. The yield is 198.1 g (95.7% of theory) of 3-hydroxybenzoic acid which has the following analysis determined by high-pressure liquid chromatography:

| 3-hydroxybenzoic acid | 99.9% |
| --- | --- |
| 2-hydroxybenzoic acid | not detectable |
| 4-hydroxybenzoic acid | not detectable |
| phenol | not detectable |
| water | 0.01% |
| NaCl | 0.1% |

EXAMPLE 2

403.9 g (91.4%), corresponding to 369 g (100%), (1.5 mols), of the dry monosodium salt of a mixture of 3-sulphophthalic acid and 4-sulphophthalic acid are added to 960 g of 50% strength sodium hydroxide solution (12 mols of NaOH), which have been initially introduced into a nickel autoclave with a capacity of 1.3 l. The autoclave is closed and kept at a temperature of 260° C. for a period of 10 hours, during which time a maximum pressure of 28 bars is set up. After the reaction has ended, the contents of the autoclave are allowed to cool, the suspension is removed and the reactor is rinsed with about 1000 ml of water. The suspension is warmed to 80° C. and introduced carefully, in the course of 1 hour, into a mixture of 1500 ml of crude concentrated hydrochloric acid and 300 g of ice, whilst stirring vigorously. Vigorous evolution of gas due to the carbon dioxide and sulphur dioxide liberated is observed. After all of the mixture has run in, residues of sulphur dioxide are driven off by warming for two hours at 90° C., and the mixture is then cooled slowly to room temperature. The crystal slurry which is filtered off is dried in a vacuum drying cabinet at 90° C. and 20 mm Hg and gives a yield of 201 g (97% of theory) of 3-hydroxybenzoic acid with a purity of 99.9%. The water content is 0.01% and the sodium chloride content is 0.1%. No other impurities are detectable.

EXAMPLE 3

246.2 g (1 mol) of a mixture of 3-sulphophthalic acid and 4-sulphophthalic acid are added, as the free acid in the form of its 50% strength aqueous solution (density 1.295 at 20° C.), to 1440 g of a 50% strength solution of sodium hydroxide (720 g of 100% = 18 mols of NaOH) in a nickel autoclave with a capacity of 3 l, and the mixture is reacted for a period of 12 hours at a temperature of 260° C. The pressure which is set up is 23 bars. After the reaction time has ended, the autoclave is allowed to cool and the contents are removed. The autoclave is rinsed with 700 ml of water and the pale grey suspension is warmed to a temperature of 80° C. and then added carefully to a mixture, which has been initially introduced, of 950 ml of 30% strength hydrochloric acid and 400 g of ice, whilst stirring. Very vigorous evolution of carbon dioxide and sulphur dioxide takes place. The cooled suspension is separated on a suction filter at room temperature and the colourless crystal cake is dried in a vacuum drying cabinet at 90° C. and 20 mm Hg for 10 hours. The yield of 3-hydroxybenzoic acid is 131 g (95% of theory) 3-hydroxybenzoic acid content 99.9%.

EXAMPLE 4

(Comparison example: melt of 3-sulphobenzoic acid to give 3-hydroxybenzoic Acid)

404.4 g of the moist monosodium salt of 3-sulphobenzoic acid (content 70%), which corresponds to 313.9 g of the monosodium salt = 283.1 g of the free acid with a molecular weight of 202.2 = 1.4 mols (obtained by sulphonation of benzoic acid), are added to 500 ml of a 50% strength solution of sodium hydroxide (actual weight 760 g, 380 g of 100% = 9.5 mols), which has been initially introduced into a 3 l nickel autoclave.

The autoclave is then closed, heated to 280° C. and kept at this temperature for a period of 6 hours.

After the reaction has gone to completion, the melt is cooled and diluted in the course of one hour, by careful addition of 500 ml of water. The diluted melt solution is added gradually to 1.5 l of aqueous hydrochloric acid (d = 1.151). Sulphur dioxide is then blown out with air in the course of 3 hours and the resulting suspension is cooled to about 15° C. The product is isolated as the moist product on a suction filter and washed with about 500 ml of water. The product is dried in vacuo.

Yield: 174.0 g of 3-hydroxybenzoic acid (90% of theory).

Composition of the 3-sulphobenzoic acid employed: 95.5% of 3-sulphobenzoic acid, 0.68% of 2-sulphobenzoic acid and 3.8% of 4-sulphobenzoic acid.

Composition of the 3-hydroxybenzoic acid obtained: 99.3% of 3-hydroxybenzoic acid, 0.25% of 2-hydroxybenzoic acid, 0.26% of 4-hydroxybenzoic acid, 0.06% of benzoic acid, 0.11% of NaCl and 0.02% of water.

What is claimed is:

1. A process for the preparation of a 3-hydroxybenzoic acid alkali metal salt which comprises contacting a sulphophthalic acid of the formula

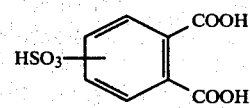

or a salt thereof with an alkali metal hydroxide in the form an alkali metal hydroxide solution having a strength of 43 to 50% by weight at a temperature in the range of 200° to 300° C. at a pressure of 10 to 30 bars.

2. A process according to claim 1, wherein the reaction is carried out at a temperature of 210° to 280° C.

3. A process according to claim 1, wherein the reaction is carried out at a pressure of 18 to 25 bars.

4. A process according to claim 1, wherein 7 to 18 mols of alkali metal hydroxide are employed per mol of sulphophthalic acid or sulphophthalic acid salt.

5. A process according to claim 1, wherein 10 to 12 mols of alkali metal hydroxide are employed per mol of sulphophthalic acid or sulphophthalic acid salt.

6. A process according to claim 1, wherein said sulphophthalic acid or sulphophthalic acid salt is in the form of an aqueous solution thereof.

7. A process according to claim 1, wherein said sulphophthalic acid or said sulphophthalic salt is in the form of a 30 to 75% by weight aqueous solution.

8. A process according to claim 1, wherein a sulphophthalic acid alkali metal salt is reacted with an alkali metal hydroxide.

9. A process according to claim 1, wherein sulphophthalic acid itself is reacted with said alkali metal hydroxide.

10. A process according to claim 1, wherein thereafter said alkali metal salt of 3-hydroxybenzoic acid is converted to 3-hydroxybenzoic acid by acidification.

11. A process according to claim 10, wherein the said acidification is carried out in an aqueous medium using a mineral acid.

12. A process according to claim 10, wherein said acidification is effected without isolation of intermediate alkali metal salt 3-hydroxybenzoic.

* * * * *

UNITED STATES PATENT AND TRADEMARK OFFICE
CERTIFICATE OF CORRECTION

PATENT NO. : 4,354,038
DATED : October 12, 1982
INVENTOR(S) : Ruthard Potthast et al It is certified that error appears in the above—identified patent and that said Letters Patent is hereby corrected as shown below:

Col. 1, line 51    Insert omitted --equation:--

Col. 2, line 26    Insert space between "15" and "hours"

Col. 2, line 32    Delete "70%" and insert --75%--

Signed and Sealed this

Twenty-eighth Day of June 1983

[SEAL]

Attest:

Attesting Officer

GERALD J. MOSSINGHOFF
Commissioner of Patents and Trademarks